(12) United States Patent
Luo et al.

(10) Patent No.: US 11,154,878 B2
(45) Date of Patent: Oct. 26, 2021

(54) MICRO-CURRENT THERAPY BEAUTY CARE SHOWER HEAD AND MICRO-CURRENT THERAPY

(71) Applicant: XIAMEN SOLEX HIGH-TECH INDUSTRIES CO., LTD., Xiamen (CN)

(72) Inventors: Weilong Luo, Xiamen (CN); Xi Huang, Xiamen (CN); Mingfu Zhang, Xiamen (CN); Wenxing Chen, Xiamen (CN)

(73) Assignee: XIAMEN SOLEX HIGH-TECH INDUSTRIES CO., LTD., Xiamen (CN)

( * ) Notice: Subject to any disclaimer, the term of this patent is extended or adjusted under 35 U.S.C. 154(b) by 61 days.

(21) Appl. No.: 16/211,427

(22) Filed: Dec. 6, 2018

(65) Prior Publication Data
US 2019/0184410 A1   Jun. 20, 2019

(30) Foreign Application Priority Data

Dec. 18, 2017   (CN) .......................... 201711368781.X
Dec. 18, 2017   (CN) .......................... 201721771454.4

(51) Int. Cl.
*B05B 1/18*   (2006.01)
*A61N 1/44*   (2006.01)
(Continued)

(52) U.S. Cl.
CPC .................. *B05B 1/18* (2013.01); *A61N 1/26* (2013.01); *A61N 1/44* (2013.01); *B05B 15/00* (2013.01)

(58) Field of Classification Search
CPC ......... B05B 1/18; B05B 1/185; B05B 5/0255; B05B 5/03; B05B 5/035; B05B 15/00;
(Continued)

(56) References Cited

U.S. PATENT DOCUMENTS 3,048,498 A * 8/1962 Marsh ..................... B05B 5/035
                                                              427/484
5,038,769 A * 8/1991 Krauser ................ A61M 15/00
                                                              128/203.27
(Continued)

FOREIGN PATENT DOCUMENTS

JP          54176288 U      12/1979
JP          3136225 B2       2/2001
(Continued)

OTHER PUBLICATIONS

The JP1OA issued Oct. 23, 2019 by the JPO.
The JP2OA issued Jun. 30, 2020 by the JPO.
The JPNOA issued Oct. 6, 2020 by the JPO.

*Primary Examiner* — Alex M Valvis
(74) *Attorney, Agent, or Firm* — Qinghong Xu

(57) ABSTRACT

This disclosure relates to a micro-current therapy beauty care shower head and a micro-current therapy. The micro-current therapy beauty care shower head includes a body, a lid, a mount and a power supply mechanism. The body has a conductive portion. The lid is connected to the cover and is provided with a water outlet portion. The mount is disposed between the lid and the cover. A first chamber is defined between the mount and the cover, and a second chamber is defined between the mount and the lid. A first through hole in communication with the water outlet is formed on the mount. The power supply mechanism is electrically coupled with the conductive portion of the body, and can generate a current, and introduce the current into water flow to be conducted to a human body through the water flow.

22 Claims, 15 Drawing Sheets

(51) Int. Cl.
 *B05B 15/00* (2018.01)
 *A61N 1/26* (2006.01)
(58) Field of Classification Search
 CPC ..... B05B 5/1691; A61M 15/02; A61M 35/25;
  A61N 1/26; A61N 1/44
 See application file for complete search history.

(56) References Cited

U.S. PATENT DOCUMENTS

| | | | | |
|---|---|---|---|---|
| 5,558,276 | A * | 9/1996 | Barrett | B05B 7/066 |
| | | | | 137/625.48 |
| 8,784,390 | B2 * | 7/2014 | Thomason | B05B 7/0838 |
| | | | | 604/289 |
| 9,486,817 | B2 * | 11/2016 | Patton | B05B 1/18 |
| 2004/0195403 | A1 * | 10/2004 | Atterbury | B05B 5/03 |
| | | | | 239/690 |
| 2005/0257515 | A1 * | 11/2005 | Song | B05B 5/008 |
| | | | | 60/202 |
| 2009/0110803 | A1 * | 4/2009 | Mather | B05D 1/06 |
| | | | | 427/8 |
| 2009/0113872 | A1 * | 5/2009 | Demmons | B05B 5/0533 |
| | | | | 60/202 |
| 2015/0273494 | A1 * | 10/2015 | Koehne | B05B 5/03 |
| | | | | 239/706 |
| 2017/0326561 | A1 * | 11/2017 | Sharratt | B05B 1/18 |

FOREIGN PATENT DOCUMENTS

| | | |
|---|---|---|
| JP | 2001169955 A | 6/2001 |
| JP | 2003174978 A | 6/2003 |
| JP | 3136225 U | 10/2007 |
| JP | 2012148058 A | 8/2012 |
| JP | 2013017667 A | 1/2013 |
| JP | 5375060 B2 | 12/2013 |
| JP | 2017217158 A | 12/2017 |
| JP | 2017217650 A | 12/2017 |
| WO | 0007658 A1 | 2/2000 |

* cited by examiner

MICRO-CURRENT THERAPY BEAUTY CARE SHOWER HEAD AND MICRO-CURRENT THERAPY

CROSS-REFERENCE TO RELATED APPLICATIONS

This application is based on and claims priority to Chinese Patent Application 201721771454.4 and 201711368781.X, filed on Dec. 18, 2017, the entire contents thereof are incorporated herein by reference.

TECHNICAL FIELD

The present disclosure relates to a field of a sanitary ware, in particular a shower head.

BACKGROUND

In order to promote texture of a skin, a plenty types of beauty care devices appear in market. The beauty care device is generally driven by an external power source, such as a battery, to move a body of the beauty care device so as to massage the skin, such that a cosmetic effect may be achieved.

However, it is required that various beauty care devices are driven by the external power sources, that is, the external power source must be provided to operate the beauty care device, thereby the beauty care devices may be usually used in an environment that is dry and distanced from water. Even if the beauty care device is driven by a battery and is attached with a water-sealing structure, there is still a risk of water ingress. In this case, such beauty care device may be operated only in a smaller amount of water, and if the beauty care device is used as showering, there will be a safety hazard to a large extent.

Therefore, how to provide a cosmetic effect for the skin as showering has become an urgent technical problem to be solved in the field.

SUMMARY

To solve the above-mentioned problem, an object of the present disclosure is to provide a micro-current therapy beauty care shower head, which may obtain a micro-current therapy beauty care effect when a user takes a shower.

For achievement of the above object, the present disclosure provides a micro-current therapy beauty care shower head including a body, a lid, a mount and a power supply mechanism. The body includes a gripping portion and a cover connected with each other, in which the gripping portion is hollow, and has a water inlet and a water outlet, and the body has a conductive portion. The lid is connected to the cover and is provided with a water outlet portion. The mount is disposed between the lid and the cover. A first chamber is defined between the mount and the cover, and a second chamber is defined between the mount and the lid. A first through hole in communication with the water outlet is formed on the mount. The power supply mechanism is electrically coupled with the conductive portion of the body, and can generate a current, and introduce the current into water flow to be conducted to a human body through the water flow.

Another aspect of the present disclosure provides a micro-current therapy, including:
providing current to a shower head;
conducting the current to the human body through the shower head; and
contacting the human body with the shower head such that the current conducted to the human body is conducted back to the shower head.

As compared with the prior art, the present disclosure has advantages below: the micro-current therapy beauty care shower head of the present disclosure combines the shower head with the beauty care device, a user holds the body of the micro-current therapy beauty care shower head, and turns on a switch of the shower head, to allow the external water source to come in, that is, may generate a micro current, so that the user may enjoy fun of the micro-current therapy while taking a shower head, and promote a shower head experience.

DETAILED DESCRIPTION

Figure 1:
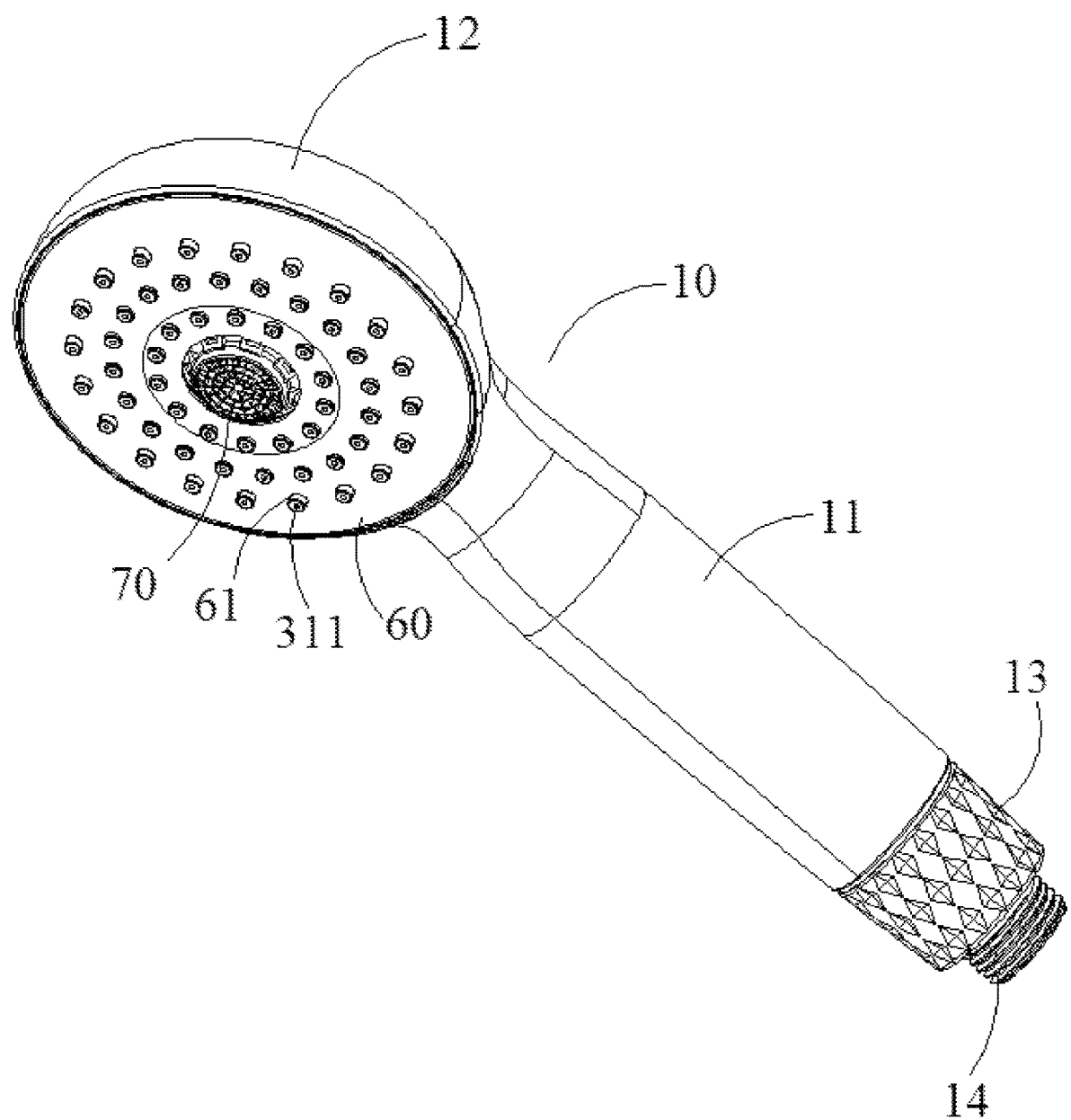
FIG. 1 is a perspective view of a micro-current therapy beauty care shower head according to the first embodiment of the present disclosure.

Now, the exemplary embodiments will be described more fully with reference to the accompany drawings. However, the exemplary embodiments can be implemented in various forms and should not be construed as limited to the embodiments set forth herein. Instead, these embodiments are provided so that this disclosure will be thorough and complete, and the concept of the exemplary embodiment will fully conveyed to those skilled in the art. In the drawings, the thickness of the regions and layers may be exaggerated for sake of clarity. Same reference signs denote the same or similar structures in the accompany drawings, and thus the detailed description thereof will be omitted.

The foresaid features, structures, or characteristics may be combined in one or more embodiments in any suitable manner. Numerous specific details as below described are provided for fully understanding the embodiments of the present disclosure. However, it will be acknowledged for the person skilled in the art that the technical solutions of the present disclosure practiced without one or more of the specific details, or by using other methods, components, materials, etc. may be employed. In other instances, well-known structures, materials, or operations are not shown or described in detail to avoid obscuring various aspects of the present disclosure.

The First Embodiment

Figure 2:
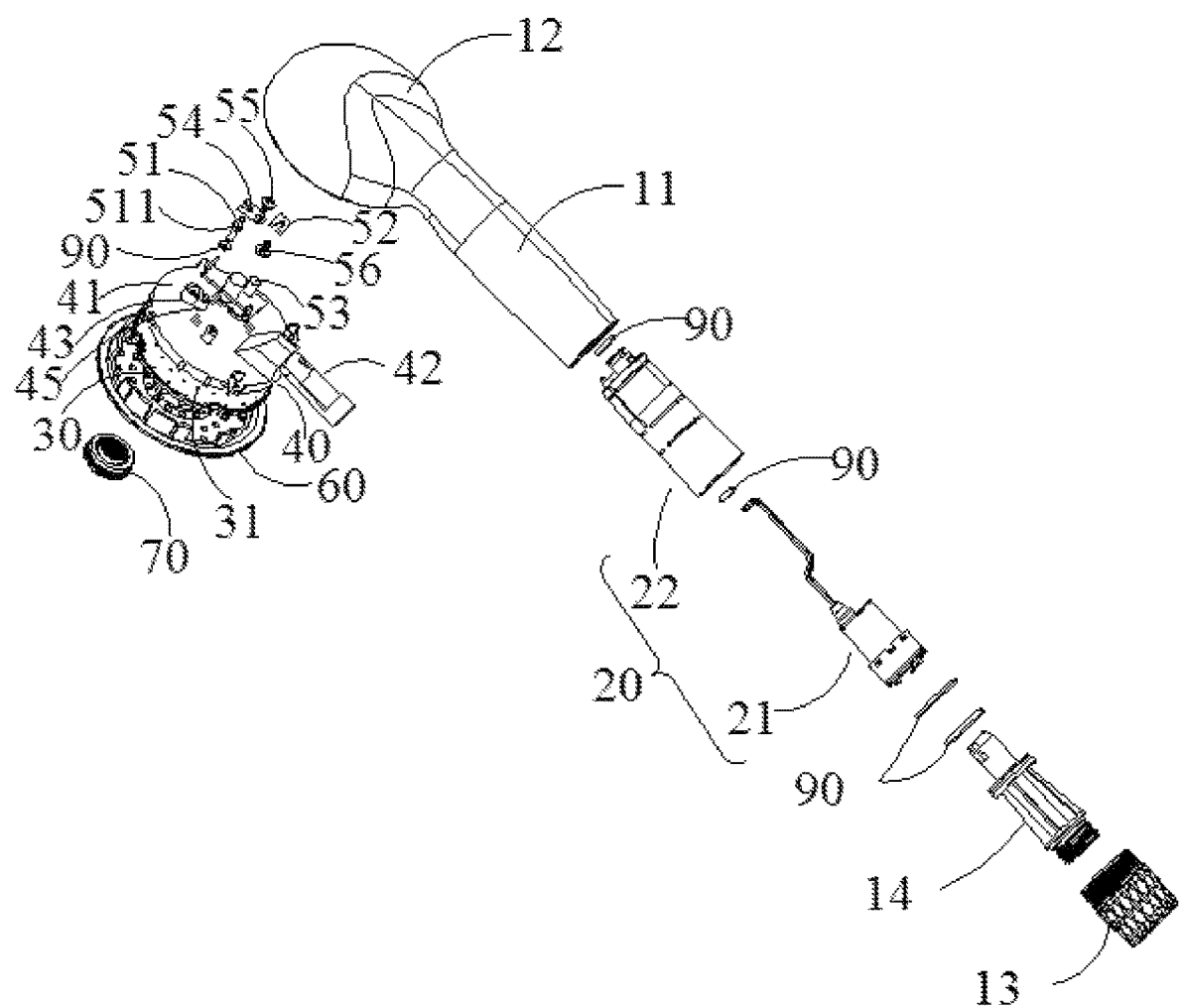
FIG. 2 is an exploded perspective view of the micro-current therapy beauty care shower head according to the first embodiment of the present disclosure.

The present disclosure provides a micro-current therapy beauty care shower head, as shown in FIG. 1 and FIG. 2, including a body 10, a lid 30, a mount 40, and a power supply mechanism.

The body 10 includes a gripping portion 11 and a cover 12 connected with each other. The gripping portion is hollow, and has a water inlet 111 and a water outlet 112. The body 10 has a conductive portion. The lid 30 is connected to the cover 12 and is provided with a water discharge portion 31.

The mount 40 is disposed between the lid 30 and the cover 12. A first chamber C1 is defined between the mount 40 and the cover 12. A second chamber C2 is defined between the mount 40 and the lid 30. The mount 40 is provided with a first through hole H1 in communication with the water outlet 112.

The power supply mechanism is electrically coupled with the conductive portion of the body 10. The power supply mechanism may generate a current and introduce the current into the water flow and conduct the current to a human body through the water flow.

Specifically, the power supply mechanism is, for example, a hydropower generating device 20. The external water source enters the hydropower generating device 20 via the water inlet 111, the hydroelectric generating device 20 generates a current, and introduces the current into the water flow. The water flow into the hydroelectric generating device 20 flows out of the micro-current therapy beauty care shower head through the water outlet portion via the water outlet 112.

Thereby, the micro-current therapy beauty care shower head of the present disclosure creatively combines the shower head with the beauty care device, a user holds the body of the micro-current therapy beauty care shower head, and turns on a switch of the shower head, to allow the external water source to come in, that is, may generate a micro current, so that the user may enjoy fun of the micro-current therapy while taking a shower head, and promote a shower head experience.

In this embodiment, the micro-current therapy beauty care shower head further includes a conductive mechanism, including a first conductive portion 51. The hydropower generating device 20 is electrically coupled with the first conductive portion 51 and the conductive portion of the body 10, respectively. The first conductive portion 51 may introduce the current from the hydropower generating device into the water flow.

Figure 3:
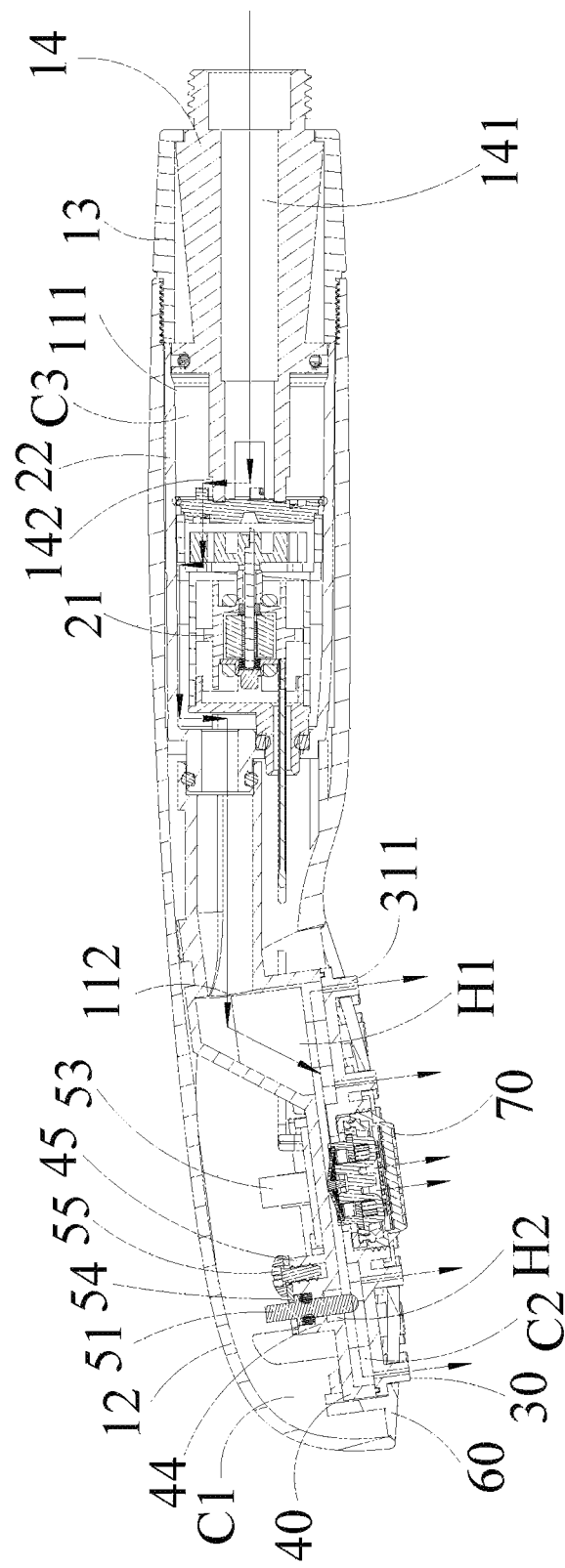
FIG. 3 is a sectional view of the micro-current therapy beauty care shower head according to the first embodiment of the present disclosure.

Wherein, as shown in FIG. 2 and FIG. 3, the conductive mechanism may further include a second conductive portion 52. The hydropower generating device 20 is electrically coupled with the conductive portion of the body 10 through the second conductive portion 52.

Figure 7:
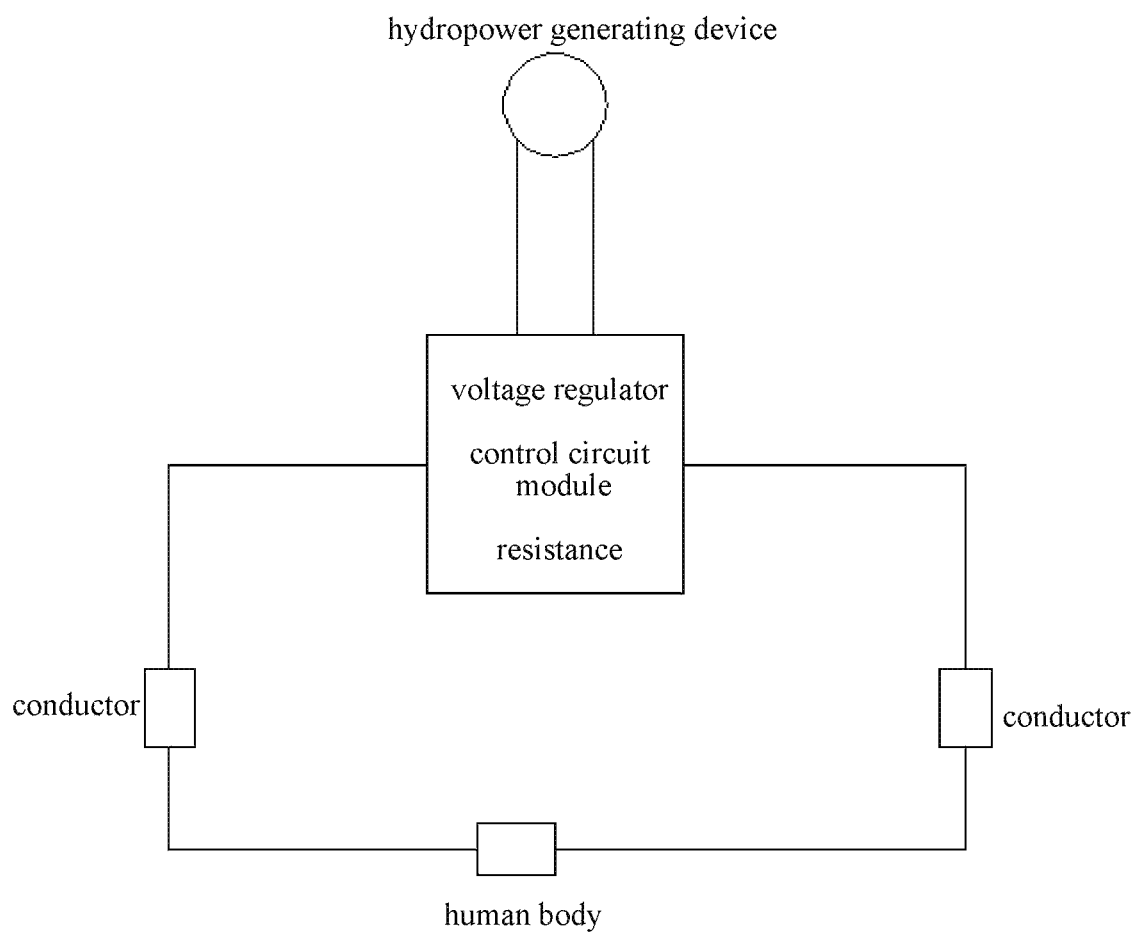
FIG. 7 is a schematic view of a circuit of the micro-current therapy beauty care shower head according to the present disclosure.

In this embodiment, the current conductive to the first conductive portion 51 is conducted with the human body through a conductor. Referring to FIG. 7, the current generated by the hydropower generating device 20 forms a complete current loop among the micro-current therapy beauty care shower head, the conductor and the human body. The current forms a micro current acceptable to the human body to contact with the human body by means of the conductor, to create a micro-current therapy effect.

In this embodiment, the conductor is water. The current generated by the hydropower generating device 20 is introduced into the water through the first conductive portion 51. The water with the current flows out of the micro-current therapy beauty care shower head via the water outlet portion 31 (as indicated by an arrow in FIG. 3) and is in contact with the human body, at the same time, the human body is in contact with the conductive portion of the body 10, such that the current carried in the water flowing out of the micro-current therapy beauty care shower head returns to a control circuit module 53 via the body 10 and the second conductive portion 52 to form a complete current loop.

In this embodiment, the water is used as a conductor for conducting micro-current between the human body and the micro-current therapy beauty care shower head. The water with the micro-current flowing out of the water outlet portion 31 is in contact with the skin of the human body, such as a face, to produce a micro-current therapy effect.

In this embodiment, as shown in FIG. 1 to FIG. 5, a third chamber C3 is provided in the interior of the gripping portion 11. The hydropower generating device 20 is located in the interior of the third chamber C3 of the gripping portion 11.

The conductive mechanism further includes a control circuit module 53 that is disposed on the mount 40 and located in the first chamber C1. The current generated by the hydropower generating device 10 is conducted to the first conductive portion 51 and the second conductive portion 52 through the control circuit module 53. The current conducted to the first conductive portion 51 is introduced into the water flow. The water flow with the current flows out of the micro-current therapy beauty care shower head via the water outlet portion 31 and is in contact with the human body, at the same time, the human body is in contact with the conductive portion of the body 10, such that the current carried in the water flowing out of the micro-current therapy beauty care shower head returns to a control circuit module 53 via the conductive portion of the body 10 and the second conductive portion 52, to form a complete current loop.

In this embodiment, both the first conductive portion 51 and the second conductive portion 52 are electrically coupled with the control circuit module 53. A part of the first conductive portion 51 is located in the first chamber C1, and another part of the first conductive portion 51 is located in the second chamber C2. The second conductive portion 52 is electrically coupled with the conductive portion of the body 10.

It should be understood that the control circuit module 53 is not limited to be disposed on the mount 40, but may be disposed at other locations of the micro-current therapy beauty care shower head, for example, the body or the lid. Moreover, in this embodiment, the control circuit module 53 has a function of converting the alternate current into the direct current, for example, into a direct current in a range of body safety current. However the control circuit module is not a necessary structure. The alternate current generated by the hydropower generating device 20 may also be transmitted to the human body and accepted by the human body. Generally, the range of the body safety current refers to a direct current less than 10 mA, or an alternate current less than 36V.

In one embodiment, the control circuit module 53 includes, for example, a circuit board and a rectifier disposed thereon. The rectifier, belonging to prior art, has a function of limiting current, therefore the description of the rectifier will be omitted in the present application. It should be understood that any structure capable of AC-DC conversion may be applied to the present disclosure.

As shown in FIG. 7, for example, the control circuit module 53 is provided with a voltage regulator for controlling the upper limit of the voltage and a resistance in series for controlling the upper limit of the current. For example, if the voltage is regulated at 3V, and the resistance is equal to 15000Ω, then the current I may be ensured to be: I<U/R=3/15000=200 µA. The voltage regulator belongs to prior art, and the description thereof will be omitted in the present application.

Wherein, the water flow enters the hydropower generating device 20 via the water inlet 111, so that the hydropower generating device 20 generates current, and the current is supplied to the control circuit module 53, and is conducted to the first conductive portion 51 and the second conductive portion 52, respectively. The current conducted to the first conductive portion 51 passes through the conductor. In this embodiment, the water is used as a conductor in communication with the human body, at the same time, the human body contacts the conductive portion of the body 10, so that the current from the conductor is guided back to the control circuit module 53 via the body 10 and the second conductive portion 52. The water flow entering the hydropower generating device 20 flows out of the micro-current therapy beauty care shower head through the water outlet portion 31 via the water outlet 112 and the first through hole 111.

In this embodiment, the water outlet portion 31 may include a plurality of water jetting nozzles 311, through which the water flow entering the second chamber C2 is ejected.

In this embodiment, the micro-current therapy beauty care shower head may further include a decorative cover 60 connected to the cover 12 and the gripping portion 11. The decorative cover 60 is provided with a plurality of decorative holes 61, the lid 30 is embedded in the decorative cover 60, and the water jetting nozzles 311 are corresponding to the decorative holes 61. The micro-current therapy beauty care shower head also includes a water softener 70 disposed in the middle of the lid 30 and protruding from the decorative cover 60.

As shown in FIG. 1, the water softener 70 is centrally disposed. The plurality of water jetting nozzles 311 are evenly distributed around the water softener 70. In use, the user may adjust water pressure of the water flow to obtain the desired a micro-current therapy massage force. It should be understood that the means for adjusting the water pressure as employed by the existing shower head may be applied to the present disclosure. The means and the technical solution of the present disclosure are combined to constitute a technical solution within the extent for protection of the present disclosure.

Figure 8:
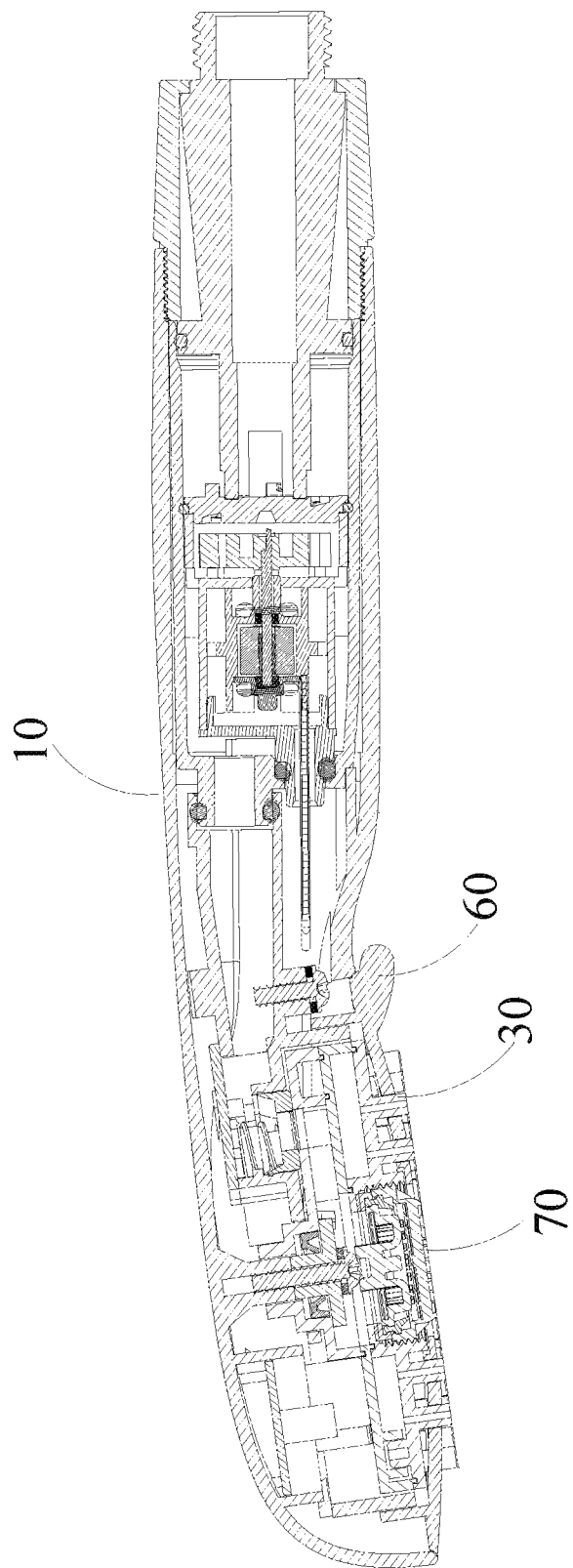
FIG. 8 is a sectional view of a multi-functional micro-current therapy beauty care shower head according to one embodiment of the present disclosure.

As shown in FIG. 8, in this embodiment, the micro-current therapy beauty care shower head is a multi-functional water outlet shower head, which may switch water jetting modes, for example, among the three modes of a separate shower head water, a separate soft water, and a mixed water, by rotating the lid 30.

Figure 9:
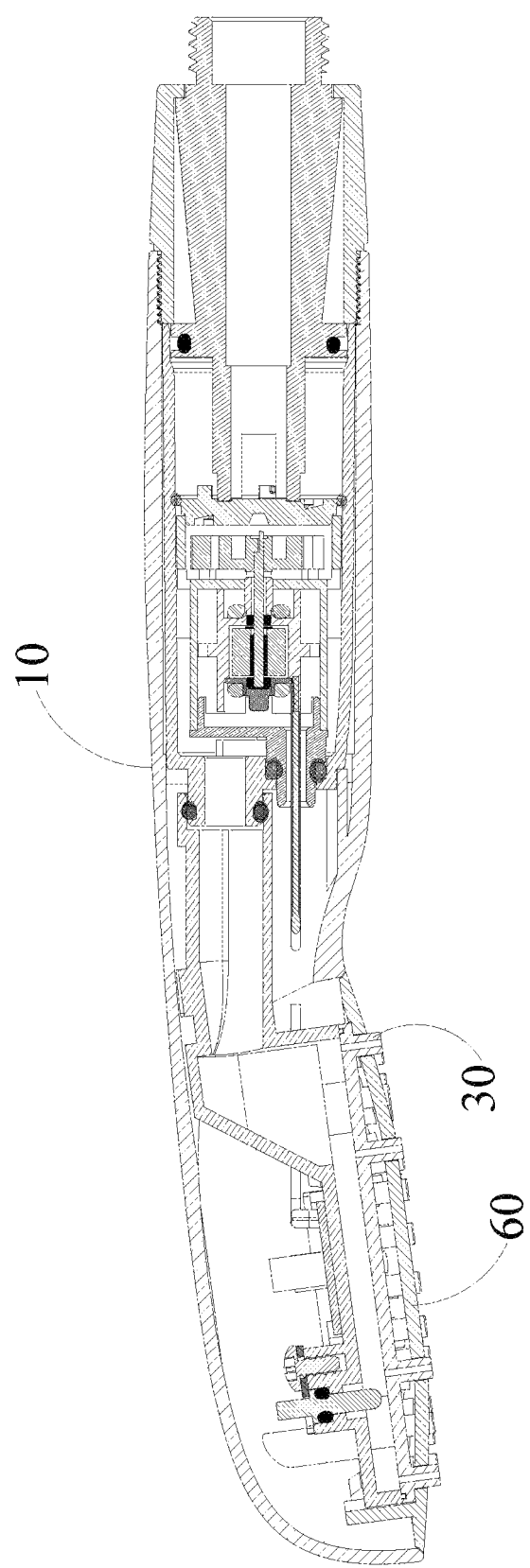
FIG. 9 is a sectional view of a single-functional micro-current therapy beauty care shower head according to one embodiment of the present disclosure.

As shown in FIG. 9, in this embodiment, the micro-current therapy beauty care shower head is a single-functional water jetting shower head, for example, only a shower head water jetting mode.

It should be understood that the water jetting modes and functions of the micro-current therapy beauty care shower head are not limited thereto, and the micro-current therapy beauty care shower head of the present disclosure may be structurally adjusted as desired to have any function of the shower heads in the prior art.

In this embodiment, as shown in FIG. 2 and FIG. 3, the mount 40 includes a fixing part 41 and a communicating part 42. The outer circumference of the fixing part 41 is connected to the lid 30. The fixing portion 41 is provided with a second through hole H2 and the first through hole H1. The control circuit module 53 is fixed to the fixing part 41, and the other part of the first conductive portion 51 passes through the second through hole H2 into the second chamber C2. Specifically, the control circuit module 53 may be welded to the fixing part 41, and also may be fixedly connected to the fixing part 41 by an electronic potting silica gel.

The communicating part 42 may be tubular, having one end abutting with the first through hole H1, and the other end protruding into the third chamber C3 and being in communication with the water outlet 112.

In this embodiment, the control circuit module 53 is, for example, a PLC, which is capable of converting the alternate current generated by the hydropower generating device 20 into a direct current to be conducted to the first conductive portion 51 and the second conductive portion 52. In this embodiment, a range of the direct current is less than 400 µA, for example, 10 µA, 100 µA, 300 µA, etc., and a range of voltage is: 1-10 V, for example, 1V, 3V, 5V, 8V, etc.

Figure 4:
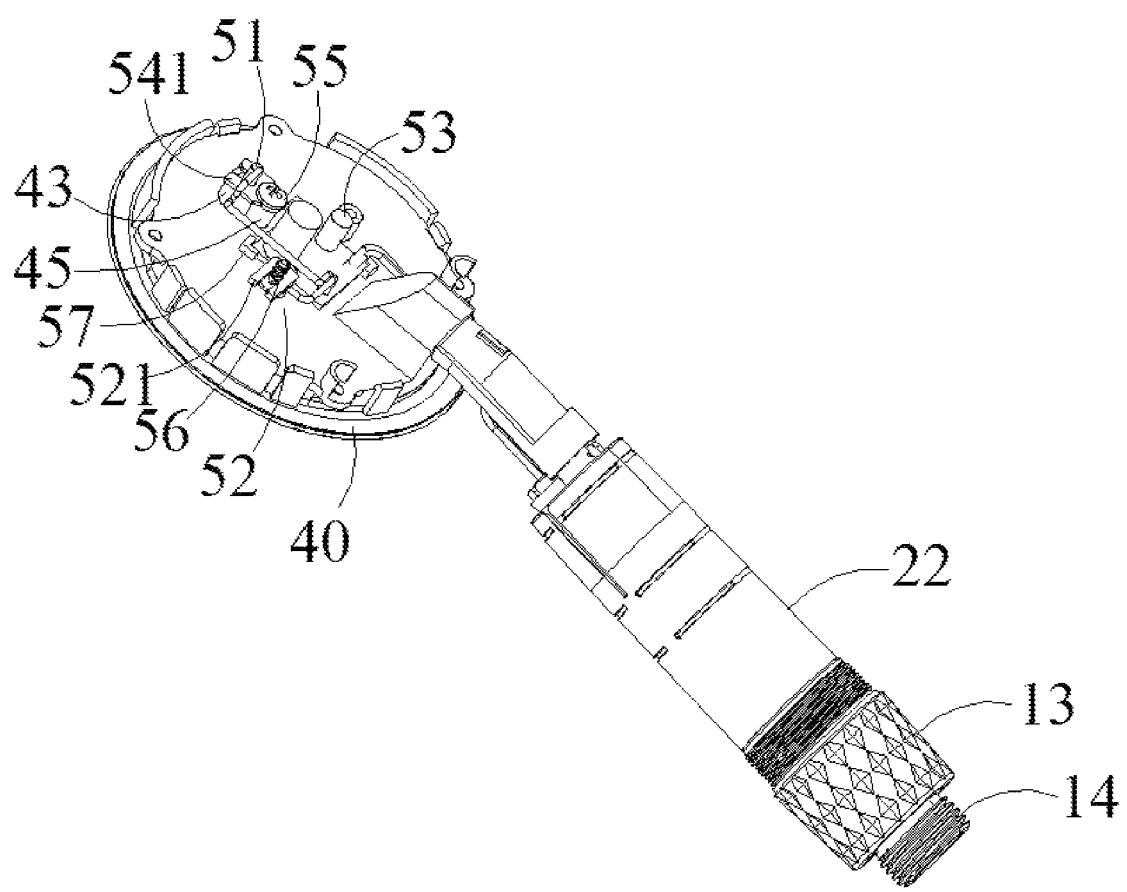
FIG. 4 is a partial perspective view of the micro-current therapy beauty care shower head according to the first embodiment of the present disclosure, wherein a body is not shown.
Figure 5:
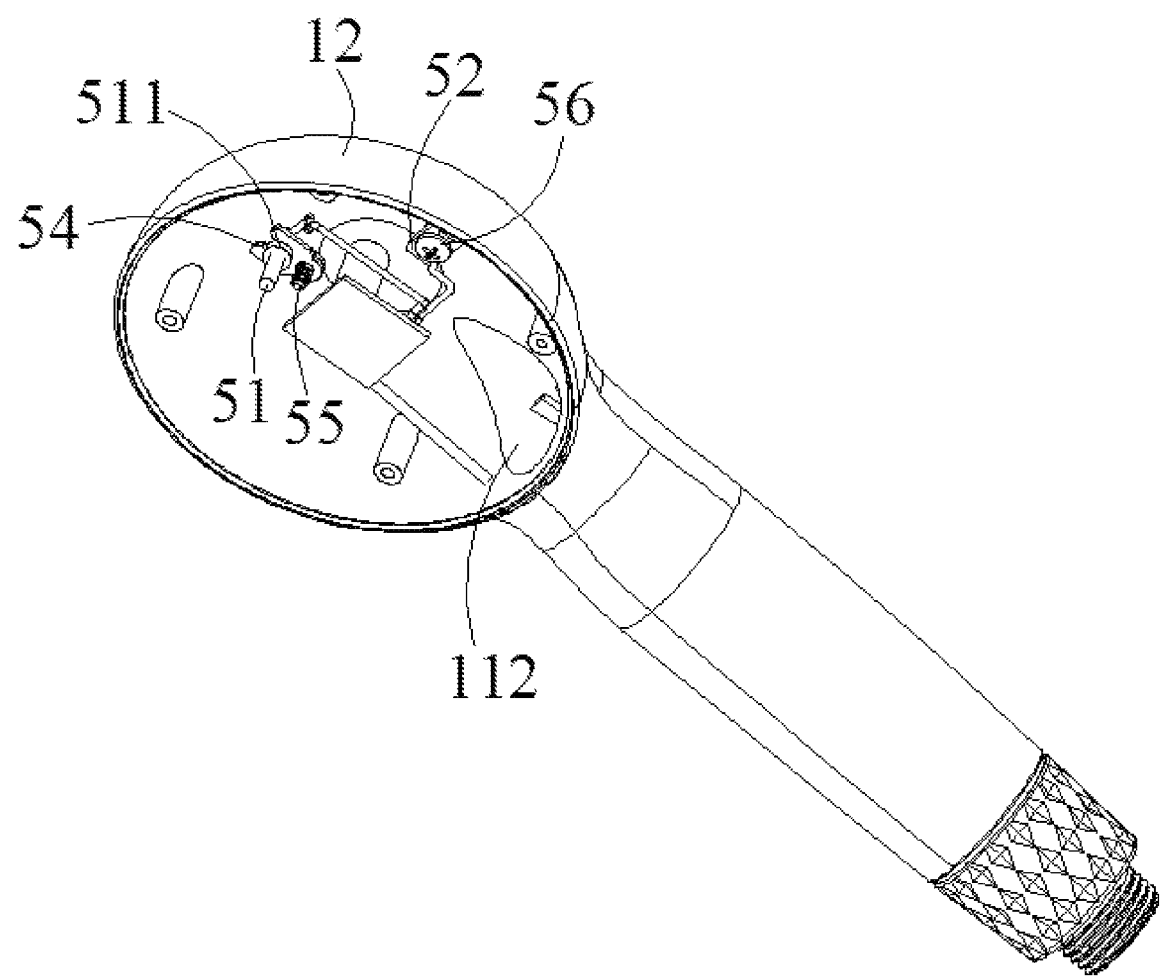
FIG. 5 is a partial perspective view of the micro-current therapy beauty care shower head according to the first embodiment of the present disclosure, wherein a mount is not shown.

As shown in FIG. 4 and FIG. 5, the first conductive portion 51 and the second conductive portion 52 are electrically coupled with the control circuit module 53 through conductive wires, respectively. The second conductive portion 52 is fixed on the inner periphery of the cover 12.

As shown in FIG. 3, the first conductive portion 51 may be a conductive pin. The fixing part 41 is provided with a hollow first stud 43. The first stud 43 is aligned with and communicated with the second through hole H2. A first flange 44 is provided on an inner edge of the first stud 43. A second flange 511 is provided on the outer circumference in the middle of the conductive pin. The conductive pin protrudes into the first stud 43 until the second flange 511 abuts against the first flange 44, so that a part of the conductive pin passes through the second through hole H2 to be positioned within the second chamber C2.

Therefore, in this embodiment, the first flange 44 is engaged with the second flange 511 of the conductive pin, and thereby playing a function of limiting the conductive pin.)

In this embodiment, the fixing part 41 is further provided with a second stud 45 with an internal thread. The conductive mechanism further includes a blocking sheet 54. The blocking sheet 54 has a pair of blocking arms 541. A screw 55 passes through the blocking sheet 54 and is screwed into the second stud 45. The conductive pin is sandwiched between the pair of blocking arms 541, and the blocking arm 541 presses against the second flange 511. As shown in FIG. 3, the second flange 511 of the conductive pin is sandwiched between the blocking sheet 54 and the first flange 44 so as to be limited in a longitudinal direction in FIG. 3, and the conductive pin is sandwiched between the pair of blocking arms 541 so as to be limited in a radial direction in FIG. 4.

In addition, a sealing ring 90 may be sandwiched between the second flange 511 of the conductive pin and the first flange 44, to prevent water in the second chamber C2 from entering the first chamber C1.

In this embodiment, as shown in FIG. 4 and FIG. 5, the second conductive portion 52 is a conductive sheet. The conductive sheet includes a pair of clamping arms 521. The conductive sheets are soldered to the conductive wires. A screw 56 passes between the pair of clamping arms 521 and is threadably connected to the inner circumference of the cover 12, such that the conductive sheet is fixedly connected to the cover 12. The connection of the screw 56 and the cover 12 is a conductive material, such that the conductive sheet is electrically coupled with the cover 12.

In this embodiment, the fixing portion 41 may further provided with a frame, which may define a mounting position of the control circuit module 53.

The above-described embodiments are only schematic illustration of the conductive mechanism. It should be understood that the structure, the position, and the connection relationship of the conductive mechanism are not limited thereto, and any mechanism for electrical conduction may be applied to the present disclosure.

In this embodiment, the gripping portion 11 and the cover 12 may be integrally formed, and have conductive materials at the interior and the exterior. As shown in FIG. 2 and FIG. 3, the body 10 may further include a first connecting portion 13 and a second connecting portion 14. The first connecting portion 13 is screwed to the gripping portion 11. The second connecting portion 14 is sleeved in the first connecting portion 13. The second connecting portion 14 has one exposed to the first connecting portion 13 for connecting a joint (not shown) of the external water source, such as a nozzle of a water pipe, and the other end abutting against the hydropower generating device 20. The second connecting portion 14 has a through water inlet passage 141, and an opening 142 is provided on the outer wall of the other end of the second connecting portion 14, thereby the external water source may enter the hydropower generating device 20 through the water inlet passage 141 and the opening 142.

In this embodiment, the hydropower generating device 20 may include a hydroelectric generator 21 and a mandrel 22. The hydroelectric generator 21 may be an existing hydroelectric generator. The water flow enters the hydroelectric generator to rotate the impeller of the hydroelectric generator, so that the hydroelectric generator generates current to be supplied to the control circuit module. Since the hydroelectric generator is an existing mechanism, which will be omitted. It should be understood that the type of hydroelectric generator is not limited thereto, and any structure that generates electric power by water flow may be applied to the present disclosure.

As shown in FIG. 3, the hydroelectric generator 21 may be sleeved in the mandrel 22. The two ends of the hydroelectric generator 21 respectively abut against the second connecting portion 14 and the mandrel 22. The two ends of the mandrel 22 respectively abut against the first connecting portion 13 and the other end of the communicating portion 42. The mandrel 22 functions to fix the hydroelectric generator 21 to improve structural stability. In addition, the third chamber C3 may have ribs therein to abut against the mandrel 22. Through cooperation of the above structure, the whole hydropower generating device 20 is stably installed in the body 10.

In addition, as shown in FIG. 2 and FIG. 3, in the whole micro-current therapy beauty care shower head, a plurality of sealing rings 90, for example, O-rings may be provided, for example, provided between the first connecting portion 13 and the second connecting portion 14, between the mandrel 22 and the communicating portion 42, and between the mandrel 22 and the hydroelectric generator 21. The cover 12, the lid 30, the mount 40, and the decorative cover 60 may also be sealing connected.

The Second Embodiment

Figure 6:
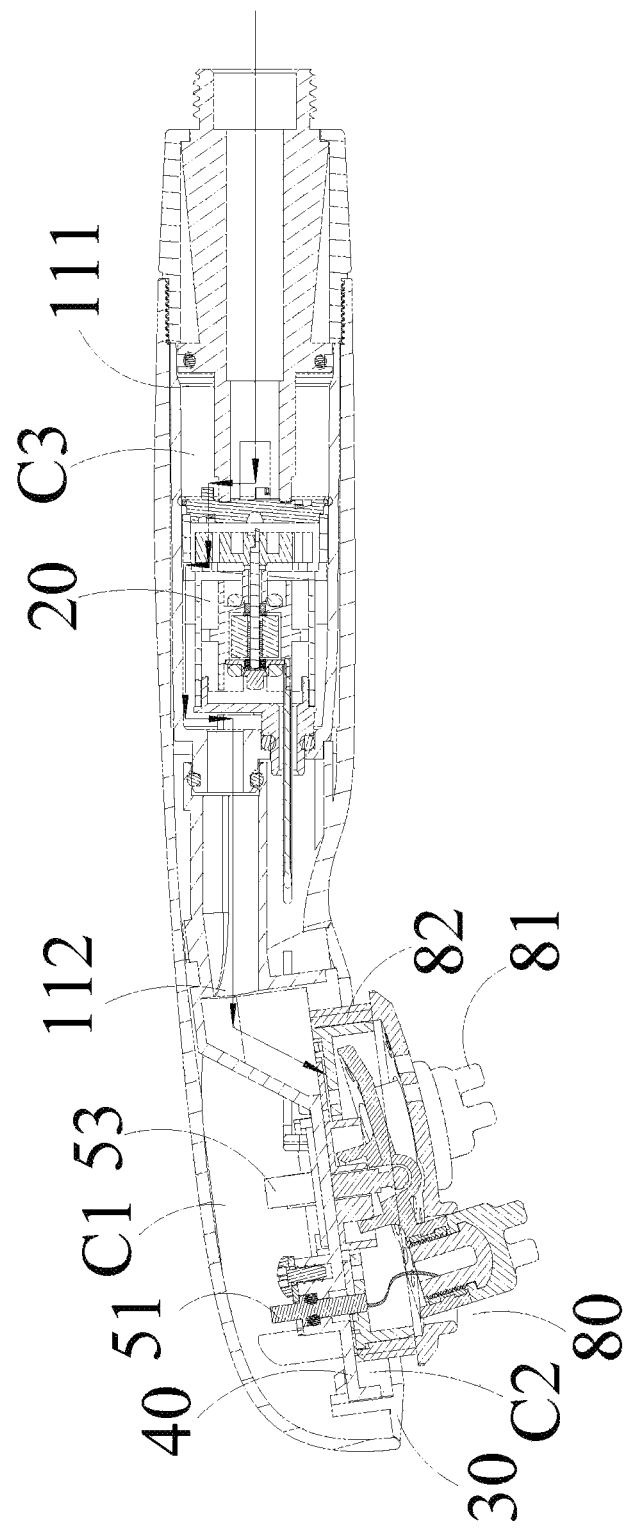
FIG. 6 is a sectional view of a micro-current therapy beauty care shower head according to the second embodiment of the present disclosure.

The second embodiment is substantially identical to the first embodiment, in addition to differences below:

As shown in FIG. 6, the micro-current therapy beauty care shower head further includes a massager 80 that is connected to the lid 30. The massager 80 includes a massage head 81. The conductor is a massage head 81 of the massager 80, which is electrically coupled with the first conductive portion 51. The first conductive portion 51 may conduct the current from the hydropower generating device 20 to the human body through the massage head 81. The massage head 81 is made of, for example, a conductive material, such as conductive silica gel.

In this embodiment, the massager 80 further includes a base 82 that is connected to the lid 30 and is partially located in the second chamber C2. The massage head 81 is movably connected to the base 82, and is electrically coupled with the first conductive portion 51 through the conductive wire.

Therefore, the first conductive portion 51 conducts current to the massage head 81, and the massage head 81 comes into contact with the human body, at the same time, the human body comes into contact with the outer housing with the conductive materials of the body 10, so that current returns to the control circuit module 53 via the body 10 and the second conductive portion 52. That is, when the shower head is held to massage by using the massage head, current is conducted to the human body through the massage head 81, and is conducted back through the body of the shower head, to form a complete current loop.

Therefore, the micro-current therapy beauty care shower head of this embodiment, in combination with an effect of the mechanical massage head and the micro-current massage, brings about more comfortable feeling for the user.

In this embodiment, the water flow entering the hydropower generating device 20 may be vented and exited through the water outlet portion 31 of the lid 30, like that described in the first embodiment, comes into contact with the human body, to play a micro-current therapy effect together with the massage head.

The Third Embodiment

The third embodiment is substantially the same as the first embodiment in addition to the differences below: the power supply mechanism is a battery.

Figure 10A:
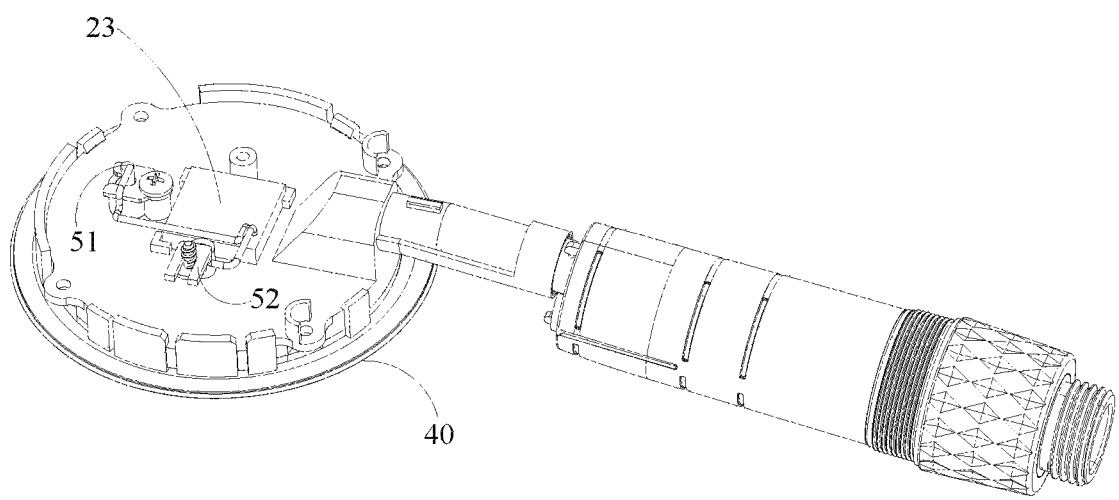
FIG. 10a and FIG. 10b are respectively a perspective view and an exploded perspective view of the micro-current therapy beauty care shower head according to the third embodiment of the present disclosure, wherein a power supply mechanism is a battery.
Figure 10B:
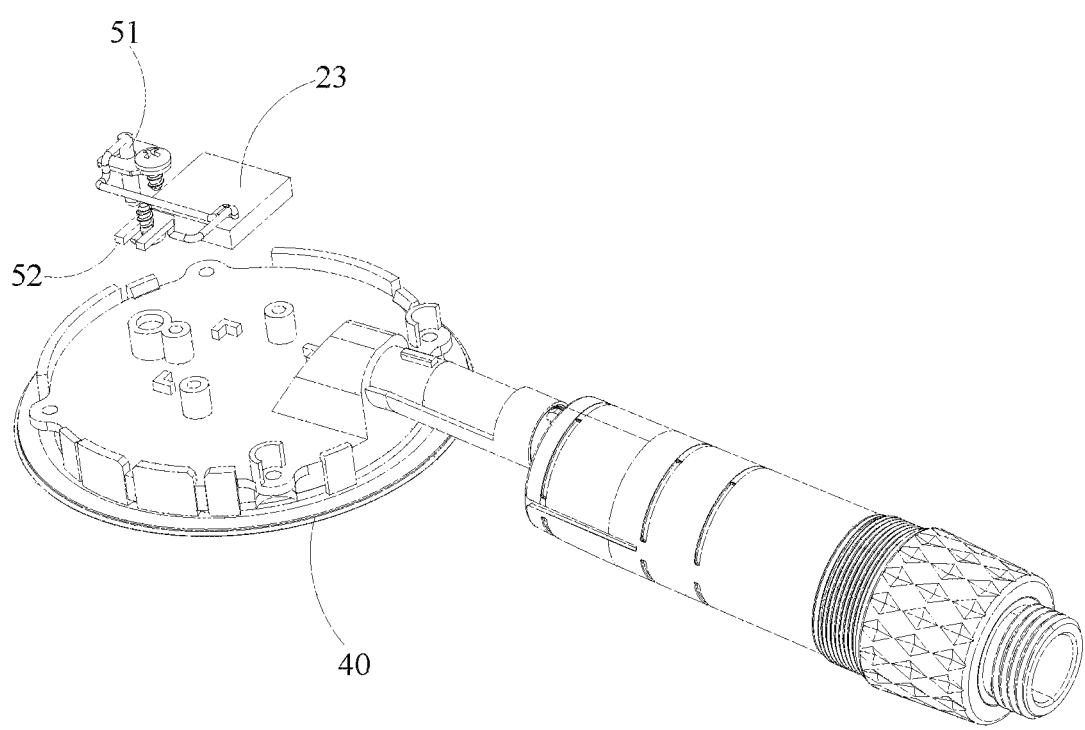
Figure 11:
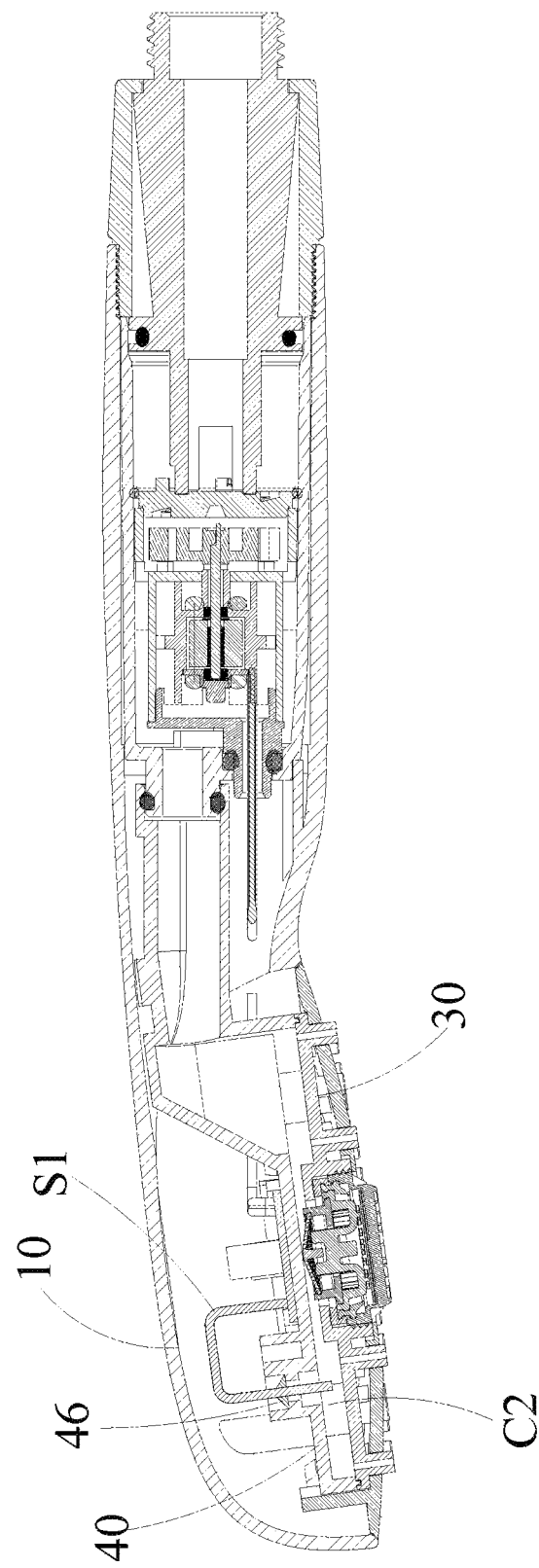
FIG. 11 is a sectional view of the micro-current therapy beauty care shower head according to the fourth embodiment of the present disclosure, wherein a conductive mechanism includes a first conductive line and a second conductive line.
Figure 12:
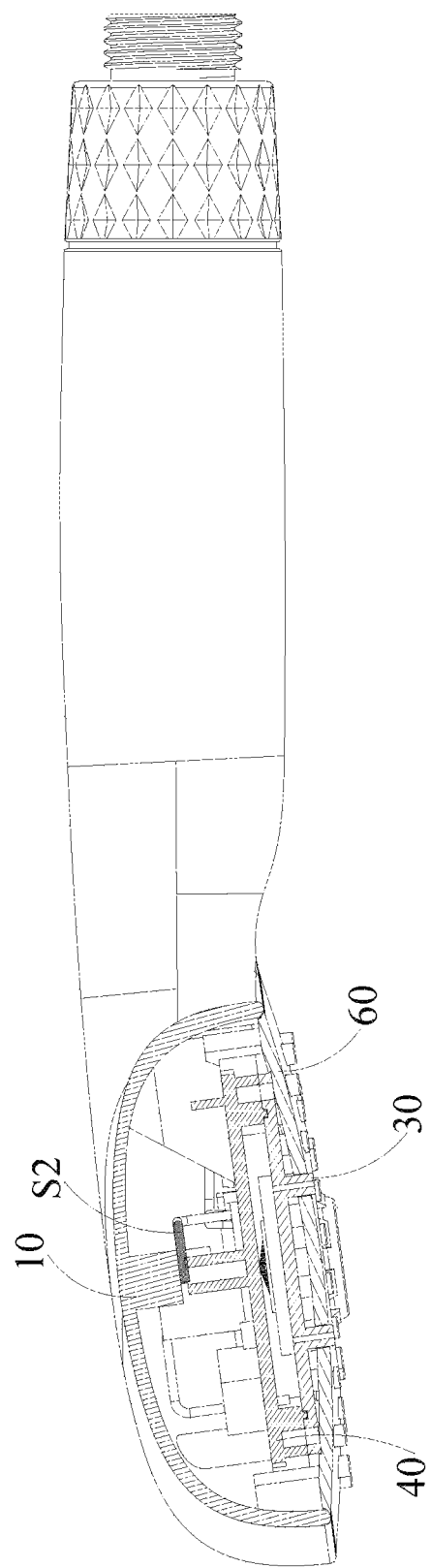
FIG. 12 is a sectional view of the micro-current therapy beauty care shower head according to the fourth embodiment of the present disclosure.
Figure 13:
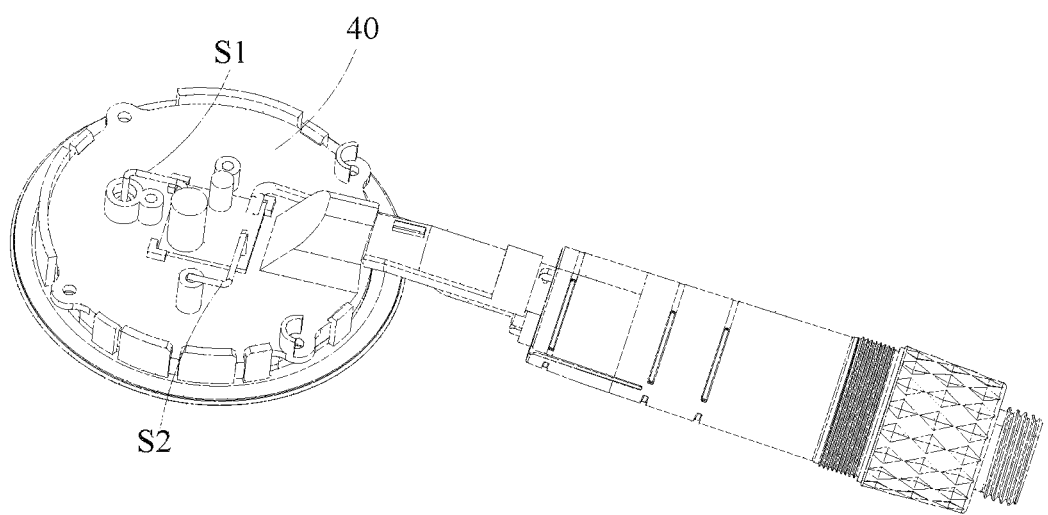
FIG. 13 is a partial perspective view of the micro-current therapy beauty care shower head according to the fourth embodiment of the present disclosure.
Figure 14:
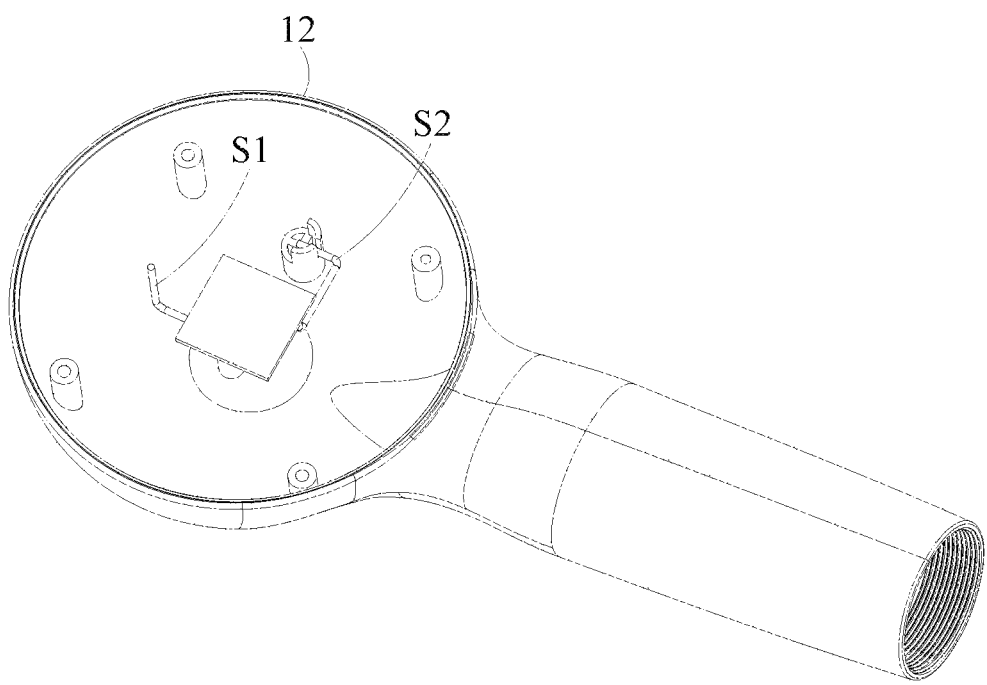
FIG. 14 is a partial perspective view of the micro-current therapy beauty care shower head according to the fourth embodiment of the present disclosure.

Specifically, as shown in FIG. 10a and FIG. 10b, the battery 23 may be mounted on the mount 40, and is electrically coupled with the first conductive portion 51 and the second conductive portion 52 through conductive wires, respectively. The structure and position of the first conductive portion 51 and the second conductive portion 52 may be substantially the same as those of the first embodiment, and thus omitted herein.

It should be understood that the power supply mechanism is not limited to hydropower generating devices and batteries, and any mechanism capable of supplying power may be applied to the present disclosure. The power supply mechanism may be placed anywhere in the micro-current therapy beauty care shower head, for example, the body or the lid.

The Fourth Embodiment

The fourth embodiment is substantially the same as the first embodiment in addition to the difference in the conductive mechanism.

Specifically, as shown in FIG. 11 to FIG. 14, the conductive mechanism includes a first conductive line S1 and a second conductive line S2. The first conductive line S1 has one end that is electrically coupled with the power supply mechanism, and the other end that passes through the hole on the mount 40 and protrudes into the second chamber C2, to be directly and electrically coupled with the water, such that the current from the power supply mechanism is introduced into the water flow. In this embodiment, the first conductive line S1 is sealed and fixed in the hole of the mount 40 by a sealant 46. The second conductive line S2 is simultaneously electrically coupled with the power supply mechanism and the conductive portion of the body 10, and is fixed to the body 10 by the mount 40. The current generated by the power supply mechanism is conducted to the conductive portion of the body 10 through the second conductive line S2, and the human body comes into contact with the conductive portion of the body, such that the current carried in the water flowing out of the micro-current therapy beauty care shower head returns to the control circuit module via the conductive portion of the body and the second conductive line S2, to form a complete current loop.

The Fifth Embodiment

This embodiment provides a micro-current therapy, including:
providing current to a shower head;
conducting current to the human body through the shower head; and
contacting the human body with the shower head so as to conduct the current conducted to the human body back to the shower head.

Wherein the step of providing current to the shower head may include: introducing water flow into the shower head, so that the hydropower generating device in the shower head generates current.

Wherein the step of conducting the current to the human body through the shower head may include conducting the current to the human body successively through the shower head and the water flow.

Wherein the step of conducting the current to the human body through the shower head may include conducting the current to the human body successively through the shower head and the massage head on the shower head.

In summary, the micro-current therapy beauty care shower head of the present disclosure creatively combines the shower head with the beauty care device, the user holds the body of the micro-current therapy beauty care shower head while shower heading, turns on the switch of the shower head to allow the external water source come in, that is, create a micro-current, thereby the user may enjoy a fun of the micro-current therapy while taking a shower head and promote the shower head experience.

Although the present disclosure has been described with reference to a few of exemplary embodiments, it should be understood that all the terms used are illustrative and exemplary, and nonrestrictive. As the present disclosure may be embodied in a variety of forms without departing from the spirit or scope of the invention, it is to be understood that the above-described embodiments are not limited to any foregoing detail. All changes and modifications within the scope of the claims or their equivalents are intended to be embraced by the appended claims.

What is claimed is:

1. A micro-current therapy beauty care shower head comprising:
a body that comprises a gripping portion and a cover connected with each other, in which the gripping portion is hollow, and has a water inlet and a water outlet, and the body has a conductive portion, the gripping portion comprises a conductive material, which formed the conductive portion;
a lid that is connected to the cover and is provided with a water outlet portion;
a mount that is disposed between the lid and the cover, a first chamber being defined between the mount and the cover, a second chamber being defined between the mount and the lid, and a first through hole in communication with the water outlet being formed on the mount;
a conductive mechanism that comprises a first conductive portion; and
a power supply mechanism that is electrically coupled with the conductive portion of the body and the first conductive portion and configured to generate a current, and introduce the current into water flow through the first conductive portion and to be conducted to a human body through the water flow, in response to that the human body is in contact with the conductive portion of the body, the current carried in the water flowing out of the micro-current therapy beauty care shower head returns to the body and the conductive mechanism to form a complete current loop.

2. The micro-current therapy beauty care shower head according to claim 1, wherein the power supply mechanism is a hydropower generating device, into which the water flow enters via the water inlet, such that the hydropower generating device generates current and introduces current into the water flow; the water flow entering the hydropower generating device flows out of the micro-current therapy beauty care shower head from the water outlet portion via the water outlet.

3. The micro-current therapy beauty care shower head according to claim 2, wherein the hydropower generating device is electrically coupled with the first conductive portion and the conductive portion of the body, respectively; and the first conductive portion can introduce the current from the hydropower generating device into the water flow.

4. The micro-current therapy beauty care shower head according to claim 3, wherein the conductive mechanism further comprises a second conductive portion; and the hydropower generating device is electrically coupled with the conductive portion of the body through the second conductive portion.

5. The micro-current therapy beauty care shower head according to claim 4, wherein the conductive mechanism further comprises a control circuit module; the current generated by the hydropower generating device is conducted to the first conductive portion and the second conductive portion through the control circuit module; the current conducted to the first conductive portion is introduced into the water flow; the water flow with current flows out of the micro-current therapy beauty care shower head via the water outlet portion, and is configured to contact the human body, at the same time, the human body is in contact with the conductive portion of the body, so that the current carded in the water flowing out of the micro-current therapy beauty care shower head returns to the control circuit module via the conductive portion of the body and the second conductive portion, to form a complete current loop.

6. The micro-current therapy beauty care shower head according to claim 5, wherein the gripping portion has a third chamber in the gripping portion interior; the hydropower generating device is located in the interior of the third chamber; the control circuit module is disposed on the mount and is located in the first chamber; both the first conductive portion and the second conductive portion are electrically coupled with the control circuit module; a part of the first conductive portion is located in the first chamber, and another part of the first conductive portion is located in the second chamber.

7. The micro-current therapy beauty care shower head according to claim 1, wherein the micro-current therapy beauty care shower head further comprises a decorative cover that is connected to the cover and the gripping portion; the decorative cover is provided with a plurality of decorative holes; the lid is embedded in the decorative cover; the water outlet portion comprises a plurality of water jetting nozzles corresponding to the decorative holes; and the water flow enters the second chamber and the is ejected from the plurality of water jetting nozzles.

8. The micro-current therapy beauty care shower head according to claim 7, wherein the micro-current therapy beauty care shower head further comprises a water softener disposed in the middle of the lid and protruding from the decorative cover.

9. The micro-current therapy beauty care shower head according to claim 3, wherein the micro-current therapy beauty care shower head further comprises a massager connected to the lid; the massager comprises a massage head that is electrically coupled with the first conductive portion; the first conductive portion can conduct the current from the hydropower generating device to the human body through the massage head.

10. The micro-current therapy beauty care shower head according to claim 9, wherein the massager further comprises a base connected to the lid and partially located in the second chamber; and the massage head is movably connected to the base, and is electrically coupled with the first conductive portion through a conductive line.

11. The micro-current therapy beauty care shower head according to claim 6, wherein the mount comprises a fixing portion and a communicating portion; an outer circumference of the fixing portion is connected to the lid; a second through hole and the first through hole are provided on the fixing portion; the control circuit module is fixed to the fixing portion, and another part of the first conductive portion passes through the second through hole into the second chamber; and the communicating portion has one end engaged with the first through hole, and the other end located in the third chamber and communicated with the water outlet.

12. The micro-current therapy beauty care shower head according to claim 6, wherein the control circuit module is capable of converting alternate current generated by the hydropower generating device into direct current to be conducted to the first conductive portion and the second conductive portion; the first conductive portion and the second conductive portion are electrically coupled with the control circuit module through conductive line, respectively; and the second conductive portion is fixed to an inner circumference of the cover.

13. The micro-current therapy beauty care shower head according to claim 12, wherein the first conductive portion is a conductive pin; the fixing portion is provided with a hollow first stud; the first stud is aligned with and communicated with the second through hole; a first flange is provided on an inner edge of the first stud; a second flange is provided on the outer circumference in the middle portion of the conductive pin; the conductive pin protrudes into the first stud until the second flange abuts against the first flange, so that a part of the conductive pin passes through the second through hole and is located in the second chamber.

14. The micro-current therapy beauty care shower head according to claim 13 wherein the fixing portion is provided with a second stud with an internal thread; the conductive mechanism further comprises a blocking sheet having a pair of blocking arms; a screw passes through the blocking sheet and screwed into the second stud; and the conductive pin is sandwiched between the pair of blocking arms; and blocking arms press against the second flange.

15. The micro-current therapy beauty care shower head according to claim 13, wherein the second conductive portion is a conductive sheet comprising a pair of clamping arms; the conductive sheet is welded to the conductive line; and a screw passes between the pair of clamping arms and is threadably connected to the inner circumference of the cover, so that the conductive sheet is fixedly connected to the cover.

16. The micro-current therapy beauty care shower head according to claim 2, wherein the gripping portion and the cover are integrally formed, and are made of conductive materials; the body further includes a first connecting portion and a second connecting portion; the first connecting portion is threadably connected to the gripping portion; the second connecting portion is sleeved in the first connecting portion; and the second connecting portion has one end exposed to the first connecting portion to connect a joint of the external water source, and the other end abutting against the hydropower generating device; the second connecting portion has a through water inlet passage, and has an opening on the outer wall on the other end, such that the external water source can enter the hydropower generating device via the water inlet passage and the opening.

17. The micro-current therapy beauty care shower head according to claim 16, wherein the hydropower generating device comprises a hydroelectric generator and a mandrel; the hydroelectric generator is sleeved in the mandrel; the two ends of the hydroelectric generator respectively abut against the second connecting portion and the mandrel; and both ends of the mandrel respectively abut against the first connecting portion and the other end of the communicating portion.

18. A micro-current therapy method comprising:
providing current to a micro-current therapy beauty care shower head of claim 1,
conducting the current to the human body through the shower head; and
contacting the human body with the shower head such that the current conducted to the human body is conducted back to the shower head.

19. The micro-current therapy method according to claim 18, wherein:
a step of providing current to the show comprises introducing water flow into the shower head, such that the hydropower generating device in the shower head generates current.

20. The micro-current therapy method according to claim 18, wherein:
a step of conducting the current to the human body through the shower head comprises conducting the current to the human body successively through the shower head and the water flow.

21. The micro-current therapy method according to claim 18, wherein:
a step of conducting the current to the human body through the shower head comprises conducting the current to the human body successively through the shower head and the massage head on the shower head.

22. A micro-current therapy beauty care shower head comprising:
a body that comprises a gripping portion and a cover connected with each other, in which the gripping portion is hollow, and has a water inlet and a water outlet, and the body has a conductive portion, the gripping portion comprises a conductive material, which formed the conductive portion;
a lid that is connected to the cover and is provided with a water outlet portion;
a mount that is disposed between the lid and the cover, a first chamber being defined between the mount and the cover, a second chamber being defined between the mount and the lid, and a first through hole in communication with the water outlet being formed on the mount;
a conductive mechanism that comprises a first conductive portion, a part of the first conductive portion is located in the first chamber, and another part of the first conductive portion is located in the second chamber, the first conductive portion is a conductive pin; and
a power supply mechanism that is electrically coupled with the conductive portion of the body and the first conductive portion and configured to generate a current, and introduce the current into water flow through the first conductive portion and to be conducted to a human body through the water flow, in response to that the human body is in contact with the conductive portion of the body, the current carried in the water flowing out of the micro-current therapy beauty care shower head returns to the body and the conductive mechanism to form a complete current loop.

* * * * *